US009033949B2

(12) United States Patent
Olesen et al.

(10) Patent No.: US 9,033,949 B2
(45) Date of Patent: May 19, 2015

(54) NEEDLE PROTECTION DEVICE

(71) Applicant: Bang & Olufsen Medicom A/S, Struer (DK)

(72) Inventors: Jan Olesen, Holstebro (DK); Bjorn Knud Andersen, Struer (DK); Esben W. Johansen, Struer (DK)

(73) Assignee: Bang & Olufsen Medicom A/S, Struer (DK)

( * ) Notice: Subject to any disclaimer, the term of this patent is extended or adjusted under 35 U.S.C. 154(b) by 167 days.

(21) Appl. No.: 13/686,277

(22) Filed: Nov. 27, 2012

(65) Prior Publication Data

US 2014/0148777 A1 May 29, 2014

(51) Int. Cl.

| | |
|---|---|
| ***A61M 5/32*** | (2006.01) |
| ***A61J 1/14*** | (2006.01) |
| ***A61J 1/20*** | (2006.01) |

(52) U.S. Cl.

CPC .............. *A61J 1/1406* (2013.01); *A61J 1/2096* (2013.01); *A61J 2001/2013* (2013.01); *A61J 2001/2051* (2013.01); *A61J 2001/2055* (2013.01); *A61J 2001/2062* (2013.01); *A61J 2001/2072* (2013.01); *A61J 2001/2075* (2013.01); *A61J 2001/2086* (2013.01)

(58) Field of Classification Search

CPC ......... A61J 1/20; A61J 1/2089; A61J 1/2093; A61J 1/2096; A61J 2001/20; A61J 2001/2013; A61J 2001/2024; A61J 2001/2055

See application file for complete search history.

(56) References Cited

U.S. PATENT DOCUMENTS

| | | | | |
|---|---|---|---|---|
| 4,200,100 | A * | 4/1980 | Willis | 604/414 |
| 6,022,339 | A | 2/2000 | Fowles et al. | |
| 7,077,835 | B2 | 7/2006 | Robinson et al. | |
| 2012/0074176 | A1 * | 3/2012 | Sullivan et al. | 222/541.2 |

FOREIGN PATENT DOCUMENTS

| | | |
|---|---|---|
| DE | 20017609 | 2/2001 |
| EP | 1776942 | 4/2007 |
| WO | W02013/076129 | 5/2013 |

OTHER PUBLICATIONS

Copy of International Search Report for PCT Patent App. No. PCT/DK2013/000079 (Apr. 2, 2014).

* cited by examiner

*Primary Examiner* — Leslie Deak
*Assistant Examiner* — Kai Weng
(74) *Attorney, Agent, or Firm* — Adam J. Cermak; Cermak Nakajima & McGowan LLP

(57) ABSTRACT

A device (2) for bringing a first vessel member (6, 26) in fluid communication with a needle member (4), which device (2) includes an adaptor (20) having a housing (14) with a holding arrangement (16, 18) configured to secure the needle (4) to the housing (14), where the housing (14) has at least a first opening (38, 40) sealed by a seal (10, 12); a cutting device (32, 34) configured to perforate the seal (10, 12). The cutting device (32, 34) is configured to perforate the seal (10, 12) and thereby break the seal (10, 12) by bringing the seal (10, 12) into contact with the cutting device (32, 34) by moving the adaptor (20) towards the vessel member (6, 26) in a manner in which the needle member (4) is not brought into contact with the seal (10, 12).

16 Claims, 12 Drawing Sheets

NEEDLE PROTECTION DEVICE

FIELD OF INVENTION

The present invention generally relates to a device for bringing a first vessel member in fluid communication with a needle member. The invention more particularly relates to a device for bringing a first vessel member in fluid communication with a sterile needle member kept in a sealed adaptor. The adaptor is preferably sealed in a manner so that the seal(s) keeps the needle sterile during storage.

PRIOR ART

It is known to use devices e.g. for reconstituting liquid for medical use. This is traditionally done by bringing together a first liquid (e.g. a diluent for reconstitution of lyophilizes medicinal drug) in a cartridge and another substance (e.g. a drug in solid form of a lyophilized medicinal drug).

Such reconstitution device is known from the US patent U.S. Pat. No. 7,077,835 that discloses a device that is configured to bring a cartridge in fluid communication with a vial by using a needle assembly having a lower and an upper sterile double-ended needle chamber both being closed by an axially slidably bung. In use the needle penetrates the bungs and hereby the needle may be damaged. The needle may bend, break or be infected with impurities and hereby no longer be suitable of being used as a reconstitution device.

Thus, there is a need for a device which reduces or even eliminates the above mentioned disadvantages of the prior art.

It is an object of the present invention to provide a device for bringing a first vessel member in fluid communication with a sterile needle member kept in a sealed adaptor, in a manner in which damaged of the needle can be prevented.

SUMMARY OF THE INVENTION

The object of the present invention can be achieved by a device having the features as defined in claim 1. Preferred embodiments are defined in the dependent sub claims and explained in the following description and illustrated in the accompanying drawings.

The device according to the invention is a device for bringing a first vessel member in fluid communication with a needle member, which device comprises:

- an adaptor having a housing comprising a holding arrangement configured to secure the needle to the housing, where the housing has at least a first opening sealed by a seal;
- cutting means configured to perforate the seal.

The cutting means are configured to perforate the seal and hereby break the seal by bringing the seal into contact with the cutting means by moving the adaptor towards the vessel member in a manner in which the needle member is not brought into contact with the seal.

Hereby it is achieved that the seal can be broken without bringing the needle member into contact with the seal. In this way damaged and contamination of the needle member can be prevented.

By the term needle member is meant a hollow needle or a hollow spike having a through-going bore with a first opening and a second opening. The needle may have at least one grinded end and thus have a bevel. The needle may be a hypodermic needle by way of example.

It is preferred that the adaptor contains a sterile needle and that the adaptor is sealed in a manner so that the seal(s) keeps the needle sterile during storage. The first vessel member may in principle be any type of vessel e.g. a vial or a cartridge by way of example.

The adaptor may be any type of assembly capable of containing the needle in a way in which the needle can be positioned and maintained in a desired position and manner.

The adaptor may by way of example have a cylindrical geometry and have a needle member extending basically along the longitudinal axis of the adaptor.

The adaptor comprises a housing comprising a holding arrangement configured to secure the needle to the housing. The housing may have any suitable geometry and the holding arrangement may be constructed in any desired way.

The seal may be any suitable seal, however, it is preferred that the seal is made in material with a small tensile strain at break—e.g. aluminium. As it will apparent from the following description, it is important that the seal will break rather than deflect, when stressed.

The cutting means may be any type of cutting means capable of perforating the seal in a desired way. The cutting means may comprise one, two or more cutting members of either equal type or of different type.

It may be an advantage that the device comprises a collar provided with protruding cutting edges and less protruding pressing edges, where the collar is configured to be mounted on or be integrated into a vessel member.

Hereby it is achieved that the cutting means can perforate the seal and hereby break the seal when the seal is brought into contact with the cutting means due to a translation of the adaptor towards the vessel member. At the same time the less protruding pressing edges can assist the process of breaking the seal in a controlled manner.

It may be an advantage that the device comprises a collar provided with protruding cutting edges and less protruding pressing edges, where the collar is configured to be mounted on or be integrated into a vessel member, where the needle member is a hollow needle or a hollow spike having at least one through-going bore having a first opening and a second opening, where the adaptor contains a sterile needle member and where the adaptor is sealed in a manner so that the seal(s) keeps the needle member sterile during storage.

It may be beneficial that the cutting means are mechanically attached to or integrated into the outside of the housing of the adaptor, where the needle member is a hollow needle or a hollow spike having at least one through-going bore having a first opening and a second opening, where the adaptor contains a sterile needle member and where the adaptor is sealed in a manner so that the seal(s) keeps the needle member sterile during storage.

It may be an advantage that the cutting means are mechanically attached to or integrated into the outside of the housing of the adaptor.

Hereby a simple and useful device can be provided. It is, by way of example possible to provide a device that merely comprises an adaptor.

In one embodiment according to the invention the cutting means are provided at the end portion of a number of flexible leg members extending from the outside of the adaptor towards the central portion of the opening of the adaptor.

It may be an advantage that the flexible legs are configured to be brought into contact with the seal when a vessel member is being pressed against the legs. Hereby a first vessel member can be brought in fluid communication with a sterile needle member kept in a sealed adaptor without damaging or contaminating the needle member.

It may be advantageous that the device comprises an adaptor having:

a first opening sealed by a first seal and a second opening sealed by a second seal.

Hereby the device may be used to provide fluid communication with a sterile needle member and two vessel members so that fluid communication can be provided between the two vessel members.

The first opening and the second opening may have basically same size and geometry; however, it is also possible that the first opening and the second opening have different size and geometry.

In a preferred embodiment according to the invention the device is configured to move the cutting means essentially along the longitudinal axis of the adaptor and hereby break the seal.

Hereby a safe, effective and easy cutting process can be carried out. The motion of the cutting means may be caused by manual action or by using an actuator of any suitable type.

It may be an advantage that the cutting means are configured to cut/break the seal approximately at the midline of the seal.

Hereby access to the needle through the central portion of the seal can be provided. In this way a centrally arranged needle can be inserted into a vessel member without bringing the needle member into contact with the seal.

In a preferred embodiment according to the invention the opening and the seal sealing the opening has a basically circular shape.

Advantageously the cutting means are configured to cut/break the seal in a manner in which only the central portion of the seal is broken.

Hereby a centrally arranged needle member can be inserted to a vessel member without bringing the needle member into contact with the seal and without risking that the peripheral portions of the seal is brought into contact with the needle member.

It may be an advantage that the needle member is arranged in the adaptor in such a way that the distance between the apex of the needle member and an end point at the periphery of the seal is more than 5%, preferably more than 10% larger than the distance between the midpoint of the seal and the end point of the seal.

Hereby it is achieved the seal is prevented from coming into contact with the needle member so that the needle member can be kept sterile both during storage of the adaptor and when the needle member is inserted into the vessel member.

It may be beneficial that the seal is circular shaped and that the needle member is arranged in the adaptor in such a way that the distance between the apex of the needle member and an end point at the periphery of the seal is more than 5%, preferably more than 10% larger than the distance between the midpoint of the seal and the end point of the seal.

Advantageously the distance between the seal and the apex of the needle member is more than 5%, preferably more than 10% of the width of the seal.

By such arrangement it is achieved that the seal is prevented from being brought into contact with the needle member. Hereby the needle member can be kept sterile both during storage of the adaptor and when the needle member is inserted into the vessel member.

It is preferred that the device is configured to maintain the apex of the needle member in a position relative to the housing of the adaptor so that a non-zero distance is kept between the apex of the needle member and the seal both when the seal is unbroken and when the seal is broken.

It may be an advantage that the needle member extends parallel to the direction of which the adaptor is configured to be moved in order to break the seal.

Hereby the needle member can be inserted into the vessel member in an effective, safe and reliable way.

It may be an advantage that the needle member has a longitudinal axis extending parallel to both the longitudinal axis of the adaptor and the longitudinal axis of the vessel member during breakage of the seal.

Hereby the needle member can be inserted into the vessel member in an appropriate and desirable way so that fluid communication between the vessel member and the needle member can be achieved.

In a preferred embodiment of the device according to the invention the device comprises means for preventing movement of the adaptor towards the vessel member and hereby causing unintended breakage of the seal.

This feature is particular desirable when the device is kept in a storing state in which no fluid communication between the vessel member and the needle member is wanted or in a situation in which only fluid communication between one of two vessel members and the needle member is desirable.

The means for preventing movement of the adaptor towards the vessel member may be mechanical means such as lock members, protrusions configured to engage in on or more corresponding indentations or any other suitable means.

It may be an advantage that the device comprises an adaptor having:

a first end with an opening, configured to be connected to a first vessel member and a second end with an opening, configured to be connected to a second vessel member, where the device is configured to be operated in a first state, in which the adaptor can be moved towards the first vessel member without moving the adaptor relative to the second vessel member, where the device further is configured to be operated in a second state following the first state, in which the adaptor can be moved towards the second vessel member without moving the adaptor relative to the first vessel.

Hereby the device can be used to carry out a predefined sequence, e.g. by bringing the needle member into contact with the first vessel member (e.g. comprising a lyophilized medicinal drug) e.g. in the first state of operation in a secure way, where the needle member will not be unintendedly brought into contact with the second vessel member (e.g. comprising a diluent for reconstituting the lyophilizes medicinal drug). When the needle member is brought into contact with the first vessel member, the second state of operation can be initiated in order to bring the other free end of the needle member into contact with the second vessel member.

Since it is of essential importance that the diluent is not spoiled/wasted accidently, it is of great value to have a device that is configured to be operated in a first state, in which the adaptor can be moved towards the first vessel member without moving the adaptor relative to the second vessel member and where the device further is configured to be operated in a second state following the first state, in which the adaptor can be moved towards the second vessel member without moving the adaptor relative to the first vessel.

It may be an advantage that the cutting means comprises two cutting edges that are configured to be arranged essentially symmetrically about the needle member when the cutting means are brought into contact with the seal.

Hereby it is possible to provide a centrally arranged opening in the seal in the area surrounding the needle member. In this way the needle member can be kept sterile.

It may be an advantage that the cutting edges are basically equal.

It may be beneficial that the adaptor comprises a housing having basically parallel walls.

The walls of the adaptor may have other forms e.g. a conical geometry by way of example.

The adaptor may comprise a housing having basically parallel walls and a base member extending essentially perpendicular to the walls of the housing.

It may be an advantage that the device comprises means for reconstituting a lyophilized medicinal drug powder contained in a first vessel member with a fluid diluent contained in a second vessel member by connecting and mixing the two substances through an adapter and where the device provides means for delivering the diluent in a controlled slow manner, in order to avoid foaming during reconstitution with the lyophilized medicinal drug powder by requiring a rotational user activation of the plunger rod actuator.

Hereby foaming can be avoided during discharge and/or filling of a vessel member.

It is preferred that a smooth, slow and controlled movement of the adaptor relative to the vessel member can be established by using the device so that a steady discharge and/or filling of a vessel member without foaming can be carried out.

It may be an advantage that the device comprises a top chassis and a button member rotably mounted in the device and being restricted from being translated/slided along the longitudinal axis of the top chassis, where the device further comprises a rod actuator slidably mounted in the device and being restricted from being rotated relative to the top chassis.

Hereby a controlled translation of the rod actuator can be provided by rotating the button member so that a controlled and steady discharge and/or filling of a vessel member without foaming can be carried out In a preferred embodiment according to the invention the device comprises a rod actuator provided with one or more protrusions configured to be guided in a track inside a button member in such a manner that the track is configured to pull the rod actuator in a first direction when the button member is rotated.

Hereby a rotation of the button member can cause a steady and controlled translation of the rod actuator so that a controlled and steady discharge and/or filling of a vessel member without foaming can be carried out.

It may be an advantage that the device comprises:

- a base having a base chassis having an open end and a lower end, which base chassis is configured to receive and contain a vessel member at its lower end;
- an adaptor containing a sterile needle member and having a first opening being sealed by a first seal and a second opening being sealed by a second seal;
- a hand operable handle configured to engage with the base while sandwiching an adaptor between the handle and the base, where the handle comprises a top chassis configured to receive and be mechanically connected to a button grip, where the handle is configured to receive and contain a syringe being sandwiched between the button grip and the top chassis, where the button comprises a rod actuator translatable mounted in the handle in a manner in which it is restricted from being rotated relative to the top chassis, where the button member rotably mounted in the handle in a manner in which it is restricted from being translated relative to the top chassis so that rotation of the button grip cause translation of the rod actuator which hereby activates syringe.

Hereby an automated, easy, safe and controlled filing sequence and empting sequence may be carried out by using the device. Such device is user friendly, reliable and easy to use.

It may be an advantage that the base chassis and the top chassis are cylindrical and configured to receive and contain a vial and/or a having a cylindrical geometry.

BRIEF DESCRIPTION OF THE DRAWINGS

The invention will become more fully understood from the detailed description given herein below. The accompanying drawings are given by way of illustration only, and thus, they are not limitative of the present invention. In the accompanying drawings.

DETAILED DESCRIPTION OF THE INVENTION

Figure 1:
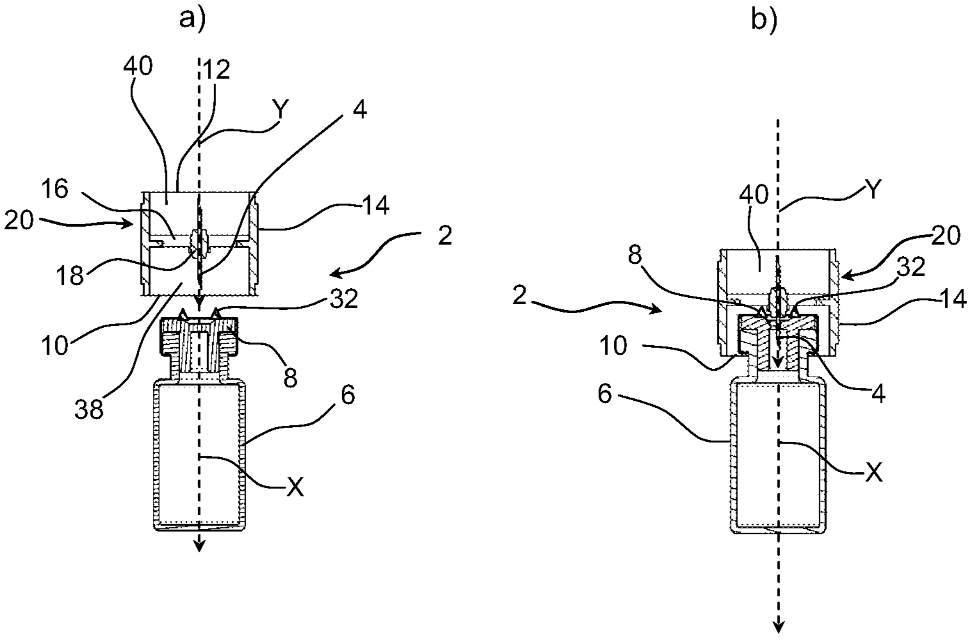
FIG. 1*a*-1*b* shows a schematic cross-sectional view of a device according to the invention.

Referring now in detail to the drawings for the purpose of illustrating preferred embodiments of the present invention, a schematically view of a device 2 of the present invention is illustrated in FIG. 1.

FIG. 1 is a schematic side view of a device 2 according to the invention. The device 2 comprises an adaptor 20 having a cylindrical housing 14 and a circular disc-shaped base member attached to the inside of the housing 14. The adaptor 20 comprises a sterile needle 4 attached to a cylindrical holding member 18 centrally arranged and attached to an aperture in the base member 16. The needle 4 extends along the longitudinal axis Y of the housing 14.

The adaptor 20 is provided with a first opening 38 sealed by a first seal 10 and a second opening 40 sealed by a second seal 12.

In FIG. 1*a*) the adaptor 20 is arranged above a vessel member 6 formed as a vial 6 having a longitudinal axis X and being sealed by a septum 8 provided with protruding cutting edges 32.

The longitudinal axis X of the vial 6 extends parallel to the longitudinal axis Y of the housing 14 of the adaptor 20.

In FIG. 1*b*) the adaptor 20 has been pushed against the vial 6. The seal 10 has been broken without bringing the needle in contact with the seal 10 and the needle has penetrated the septum 8 of the vial 6. Thus, the needle 4 has been brought into fluid communication with the vial 6 without bringing the needle 4 into contact with the seal 10. Accordingly, to the needle 4 is kept sterile and is being protected from damage and contamination during the breakage of the seal 10.

Figure 2:
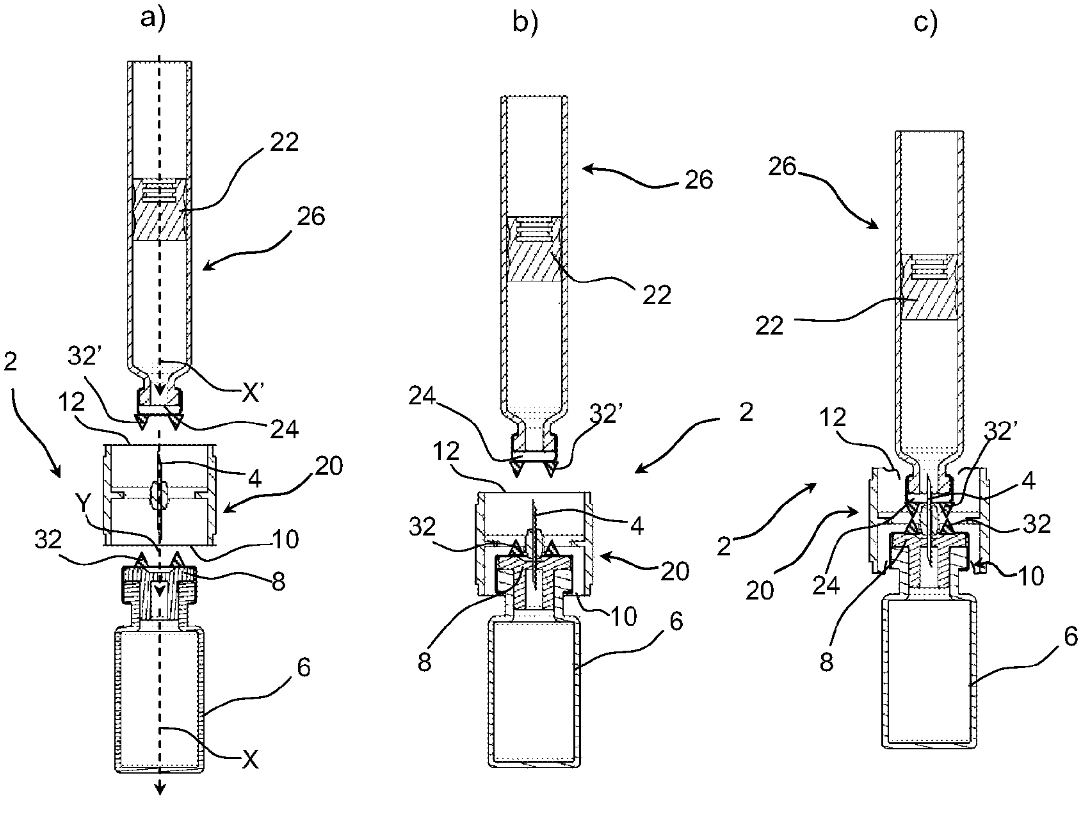
FIG. 2*a*-2*c* shows another schematic cross-sectional view of the device shown in FIG. 1.

FIG. 2 illustrates another schematic cross-sectional view of a device similar to the one shown in FIG. 1. The device 2 comprise the same features as illustrated in FIG. 1, however, an additional cartridge 26 sealed with a septum 24 and being provided with a plunger 22 is provided above the adaptor 20. The septum 24 of the cartridge 26 is provided with cutting edges 32 configured to break the seal 12 of the adaptor 20.

In FIG. 2 *a*) the cartridge 26 is arrange above the adaptor 20 which is arranged slightly above the vial 6. Thus, the first seal 10 and the second seal 12 are kept undamaged.

In FIG. 2*b*) the adaptor 20 has been pushed against the vial 6 and the cutting edges 32 provided at the septum 8 of the vial 6 have penetrated and hereby caused a breakage of the first seal 10 of the adaptor 20. The needle 4 has been inserted into the vial 6 through the septum 8. Accordingly, fluid communication has been established between the needle 4 and the vial 6. The cartridge 26 on the other hand is remained in the same distance above the adaptor 20.

In FIG. 2*c*) the cartridge 26 has been pushed against the seal 12 of the adaptor 20. The cutting edges 32' provided at the septum 24 of the cartridge 26 have penetrated the seal 12 of the adaptor 20. Accordingly, an aperture has been created in the seal 12 so that the needle 4 has been given access to the septum 24 of the cartridge 26. The needle 4 has penetrated the septum 24 of the cartridge 26 and hereby fluid communication has been established between the needle 4 and the cartridge 26.

It can be seen that the cutting edges 32 of the vial 6 penetrates the first seal 10 of the adaptor 20 by moving the adaptor 20 along its longitudinal axis Y towards the vial 6 and thus along the longitudinal axis Y of the vial 6. In the same manner the cutting edges 32' of the cartridge 26 penetrate the first seal 10 of the adaptor 20 by moving the adaptor 20 along its longitudinal axis Y towards the vial 6 and thus along the longitudinal axis Y of the vial 6. In the same manner the cutting edges 32' of the cartridge 26 penetrates the second seal 12 of the adaptor 20 by moving the cartridge 26 along its longitudinal axis X towards the adaptor 20 and thus along the longitudinal axis Y of the adaptor 20.

Figure 3:
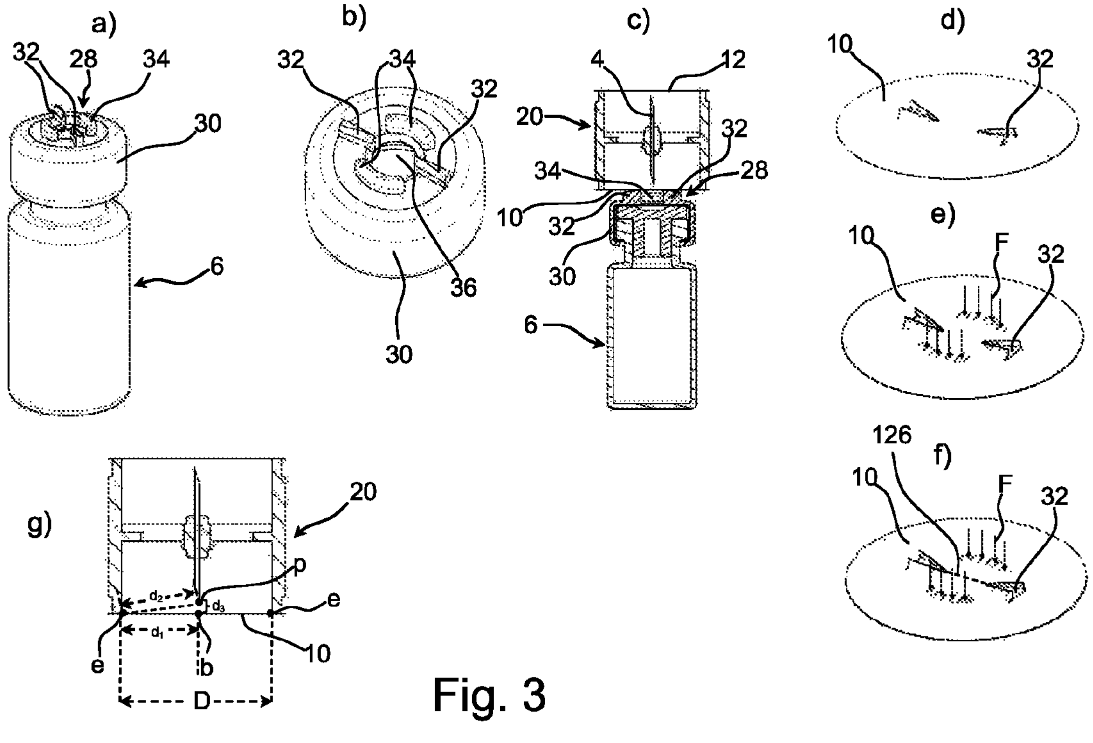
FIG. 3*a*-3*f* shows different perspective and cross-sectional views of parts of a device according to the invention.

FIG. 3*a*) illustrates a perspective view of a vial 6 according to the invention. The vial 6 comprises a basically cylindrical collar 30 mechanically attached to the top portion of the vial 6. On the upper surface 28 of the collar 30 two protruding cutting edges 32 and two less protruding pressing edges 34 are provided.

FIG. 3*b*) illustrates a close-up perspective view of the collar 30 shown in FIG. 3*a*). It can be seen that the collar 30 comprises a circular centrally arranged aperture 36 configures to receive a needle 4 of an adaptor 20.

In FIG. 3*c*) an adaptor 20 is being brought into contact with the vial 6. It can be seen that the cutting edges 32 touches the outer surface of the seal 10 of the adaptor 20 while there is a non-zero distance between the seal 10 and the pressing edges 34.

FIG. 3*d*) illustrates the seal 10 seen from the outside of the adaptor 20 while the two cutting edges 32 are brought into contact with the seal 10.

In FIG. 3*e*) the cutting edges has are penetrating the seal 10 while the pressing edges 34 are brought into contact with the seal 10.

In FIG. 3*f*) the seal 10 begins to break along the central portion of the midline 126 of the seal 10. The force F exerted by the pressing edges 34 towards the seal 10 is indicated.

FIG. 3*g*) illustrates a cross-sectional view of an adaptor 20 according to one embodiment of the invention. It can be seen that the seal 10 is arranged in a non-zero distance $d_3$ from the apex p of the needle 4 so that the seal 10 is not being brought into contact with the needle 4.

The distance $d_1$ between the end point e (at the periphery of the seal 10) and the break point b (corresponding to the midpoint of the seal 10) is smaller than the distance $d_2$ between the end point e (at the periphery of the seal 10) and the apex p of the needle 4. Moreover it can be seen that the width D of the seal 10 corresponds to two times the distance $d_1$ between the end point e and the break point b.

It is preferred that needle 4 is arranged in the adaptor 20 in such a way that the distance $d_2$ between the apex p of the needle 4 and an end point e at the periphery of the seal 10 is more than 5%, preferably more than 10% larger than the distance $d_1$ between the midpoint b of the seal 10 and the end point e of the seal.

In this way the seal 10 is prevented from coming into contact with the needle 4. Accordingly, the needle 4 can be kept sterile both during storage of the adaptor 20 and furthermore damage of the needle 4 during insertion of the needle 4 into a vessel member 6 can be avoided.

It is preferred that the distance $d_3$ between the seal 10 and the apex p of the needle 4 is larger than 5%, preferably larger than 10% of the width D of the seal 10.

Figure 4:
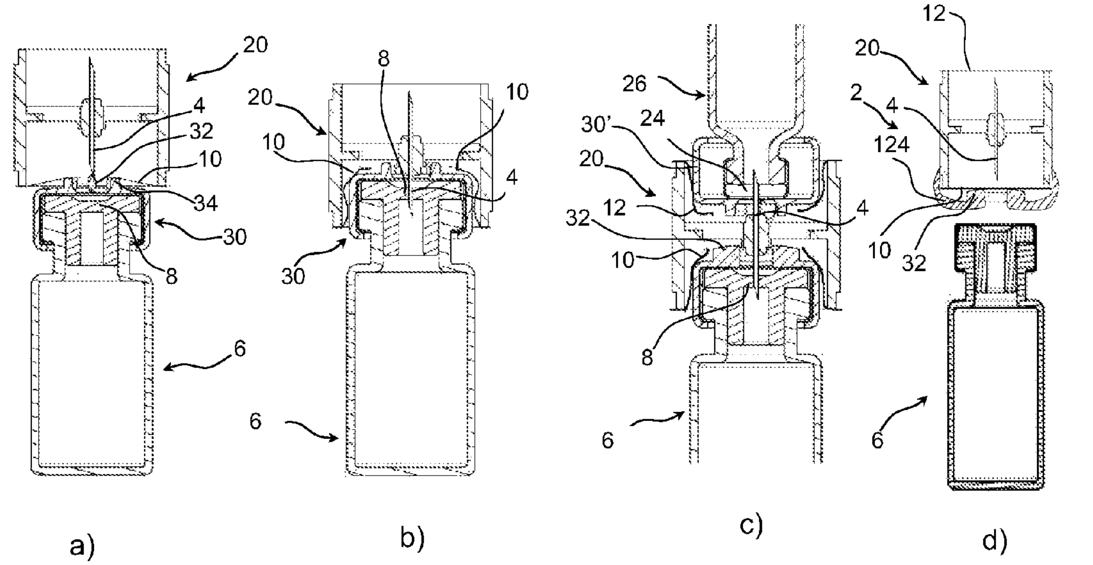
FIG. 4*a*-4*d* shows cross-sectional views of two different embodiments according to the invention.

FIG. 4*a*), FIG. 4*b*) and FIG. 4*c*) illustrates a cross-sectional view of a device 2 according to the invention. The device 2 comprises an adaptor 20 corresponding to the one shown in FIG. 1-3.

In FIG. 4*a*) the collar 30 of the vial 6 is being pressed against the seal 10 of the adaptor 20. It can be seen that an aperture has been created in the seal 10 so that the needle 4 can be inserted into the vial 6.

In FIG. 4*b*) the needle 4 has been inserted into the vial 6. It can be seen that the needle 4 has penetrated the septum 8 of the vial 6.

In FIG. 4*c*) the needle 4 has been brought into fluid communication with a vial 6 and with a cartridge 26. The first seal 10 has been broken by the cutting edges 32 of the collar 30 of the vial. Moreover, the second seal 12 has been broken by the cutting edges (not shown) of the collar 30' of the cartridge 26.

FIG. 4*d*) illustrates an alternative embodiment of a device 2 according to the invention. The device 2 comprises an adaptor 20 having two arms 124. Cutting edges 32 are provided at the distal end of the arms 124 and the arms 124 are mechanically attached to the outside of the housing of the adaptor 20 at their proximate end. A vial 6 is arranged below the adaptor 20. When the vial 6 is pressed against the arms 124 of the adaptor 20 the cutting edges 32 will penetrate the seal 10 of the adaptor 20 and hereby break the seal 10 so that the sterile needle 4 has free access to the vial 6 without being touched by the seal 10.

The embodiment shown in FIG. 4*d*) is simple and easy to use. Arms 124 similar to the ones shown may also be provided at the other end of the adaptor 20 so that these arms (not shown) can penetrate the other seal 12 of the adaptor 20 so that the needle 4 can be inserted into another vessel member (not shown).

The arms 124 are preferably flexible so that the cutting edges 32 may be moved relative to the housing of the adaptor 20. The arms 124 may be hinged to the outside of the housing of the adaptor 20. The arms 124 may also be integrated into the adaptor 20. The arms 124 may be mechanically connected to the outside of the housing of the adaptor 20 by other suitable means.

Figure 5:
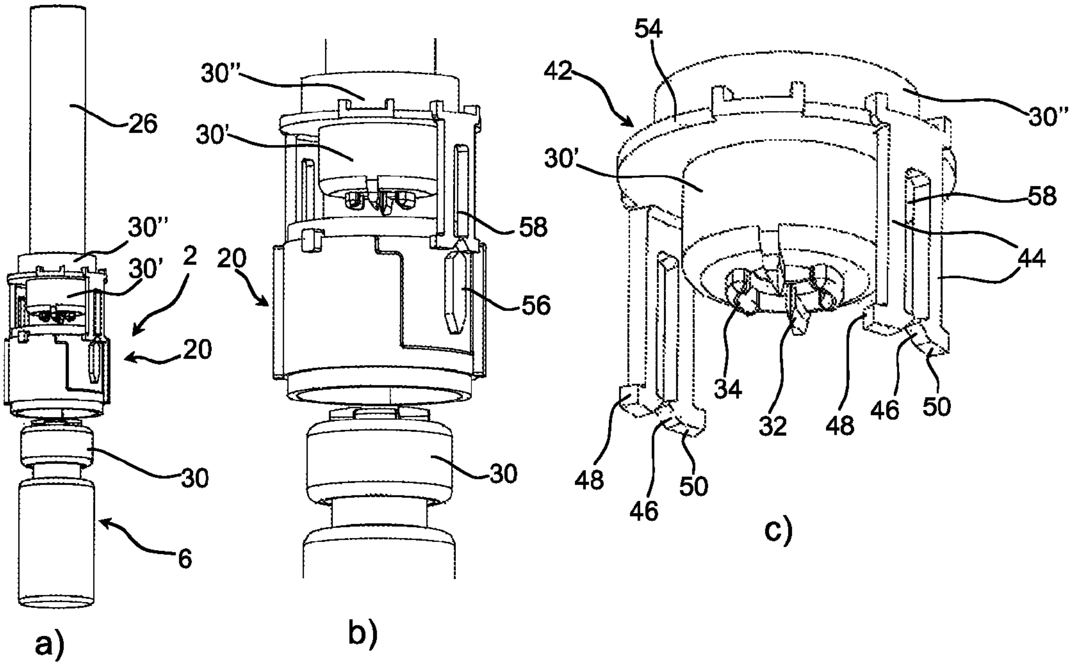
FIG. 5*a*-5*c* shows perspective views of a device configured to perform a controlled sequence.

FIG. 5 illustrates schematic perspective views of a device 2 according to the invention. The device 2 comprises an adaptor 20 and means for performing a predefined sequence. A cartridge 26 provided with a collar 30' is being moved towards the adaptor 20 while a vial 6 provided with a collar 30 is arranged below the adaptor 20. The device 2 comprises an interface 42 comprising a plate member 54 and two members each having two beams 44 extending along the length of the adaptor 20 are attached to a collar member 30" surrounding the cartridge 26.

A space 58 is provided between the beams 44. The device 2 comprises a rib 56 that is configured to be contained in the space 58 so that the beam 44 can be axially fixed relative to the rib 56.

Each of the beams 44 are provided with end members having an angled surface 46, a side surface 48 and a front surface 50. It can be seen that the collar 30' is provided with cutting edges 32 as well as pressing edges 34.

Figure 6:
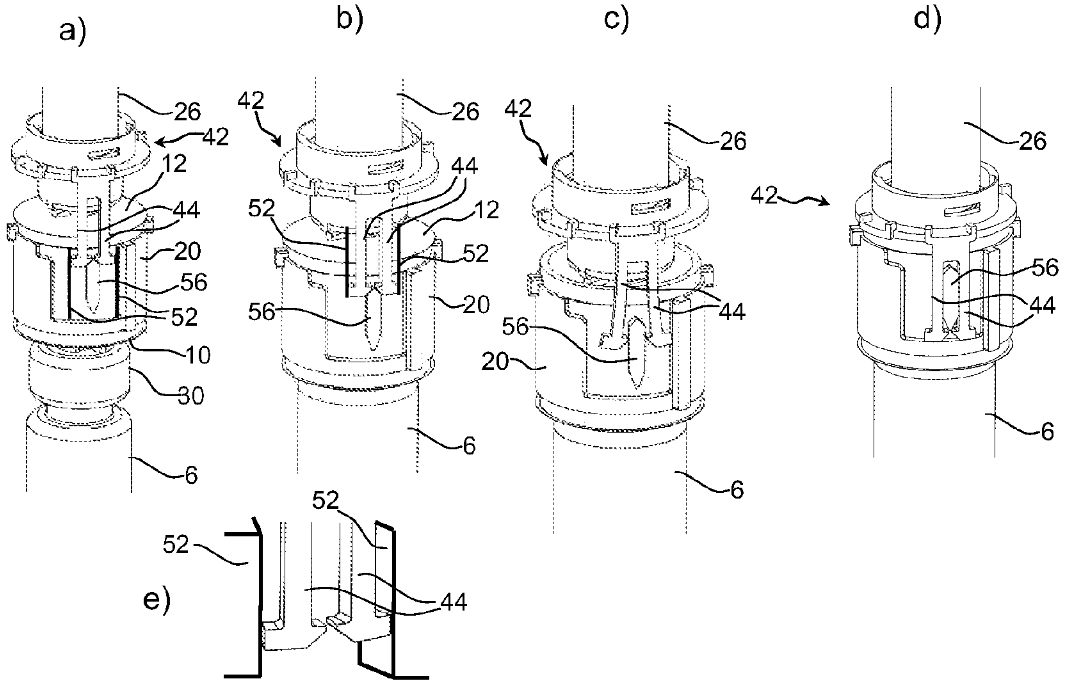
FIG. 6*a*-6*e* shows a number of perspective views of a device capable of performing an automated sequence.

FIG. 6 illustrates several perspective views of a device according to the invention. A cartridge 26 is connected to an interface 42 like the one shown in FIG. 5. It can be seen that the adaptor 20 is sealed by a first seal 10 and a second seal 12 and that motion of the cartridge 26 towards the adaptor 20 will cause breakage of the seal 12.

During the steps shown in FIG. 6*a*) and FIG. 6*b*) the beams 44 are guided within two rail members 52. When the beams 44 are guided within two rail members 52 the beams 44 cannot be moved away from each other and deflect (like shown in FIG. 6*c*). Therefore, the cartridge 26 cannot be slided towards the adaptor 20 when the beams 44 are guided within two rail members 52. In FIG. 6*a*) and FIG. 6*b*) the cartridge 26 will push against the adaptor 20 and herby move the adaptor towards the vial 6 so that the seal 10 of the adaptor 20 will break like shown in FIG. 1-4.

On the other hand, when the collar 30 of the vial 6 has been fully inserted into the adaptor 20, a further press of the cartridge 26 towards the adaptor 20 will result in a situation like the one illustrated in FIG. 6*c*). In FIG. 6*c*) the beams 44 are no longer guided within the two rail members 52 (like shown in FIG. 6 and in FIG. 6*b*). Therefore, further motion of the cartridge 26 towards adaptor 20 will cause the rib to enter the space between the beams 44 so that the beams 44 will be moved away from each other. When the cartridge 26 is moved further towards the vial 6 the rib 56 will be fully contained within the space between the beams 44 like illustrated in FIG. 6*d*).

FIG. 6*e*) illustrates a perspective close-up view of the beams 44 being guided with in two rail members 52.

Figure 7:
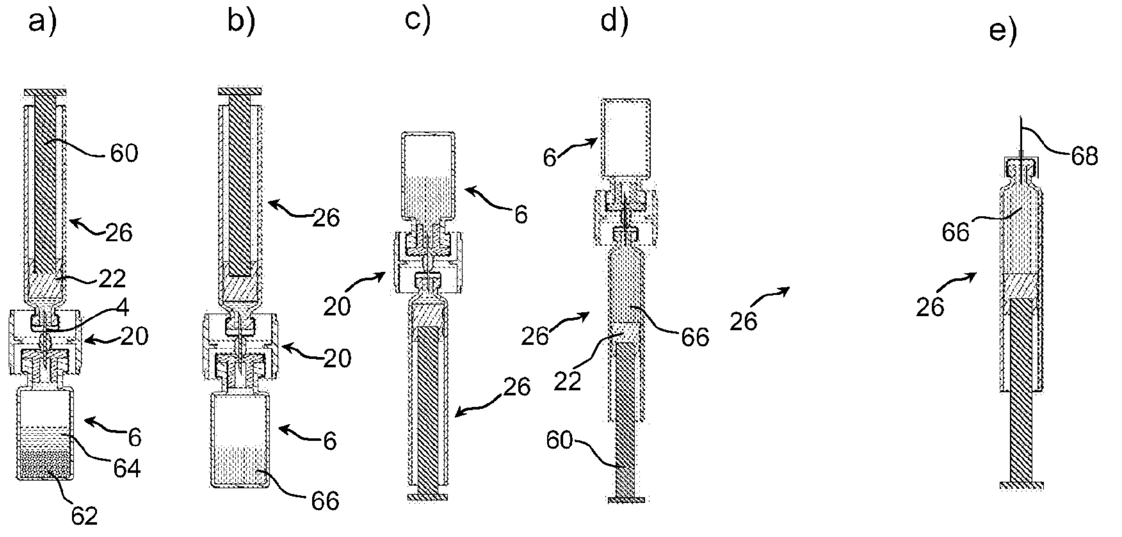
FIG. 7*a*-7*e* shows cross-sectional views of two different embodiments according to the invention.

FIG. 7 illustrates a sequence where the device according to the invention is being used. In FIG. 7*a*) a cartridge 26 is brought into fluid communication with the needle 4 of the adaptor 20. The adaptor 20 has further been brought into fluid communication with a vial 6. The plunger rod 60 is pressed into the cartridge 26 and a first substance 64 is being filled into the vial 6. A second substance 62 is already filled into the vial 6. The first substance 64 may be a diluent for reconstitution of lyophilizes medicinal drug and the another substance 62 is a drug in solid form of a lyophilized medicinal.

In FIG. 7*b*) the first substance 64 and the second substance 64 are mixed into a third substance 66.

In FIG. 7*c*) the arrangement is turned upside down.

In FIG. 7*d*) the mixed substance 66 has been sucked out of the vial 6.

In FIG. 7*e*) the adaptor 20 and the vial 6 have been removed and the cartridge 26 is filled with the mixed substance 66 and is ready for being used to injection of the mixed substance 66.

Figure 8:
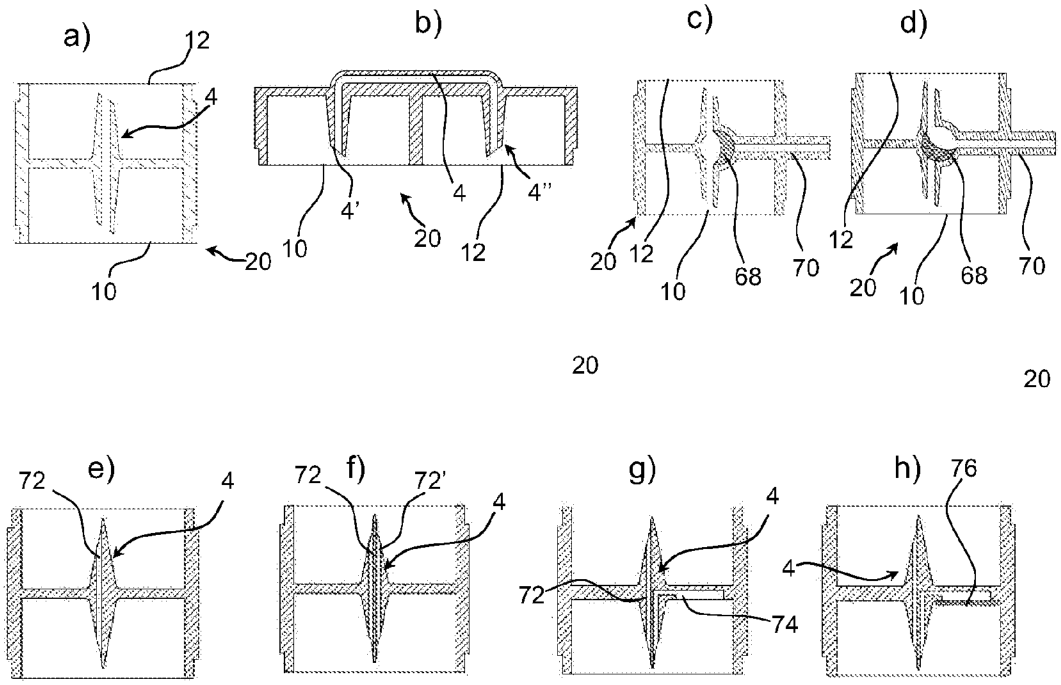
FIG. 8*a*-8*h* shows a number of cross-sectional views of needle members according to the a device according to the invention.

FIG. 8 illustrates cross-sectional views of various embodiments of a needle member 4 according to the invention.

FIG. 8*a*) illustrates a needle 4 that is integrated into the adaptor 20 (e.g. by a plastic moulding process).

FIG. 8*b*) illustrates a needle member 4 having two needle members 4', 4" arranged in the same level and pointing towards the same plane. The two needle members 4', 4" are connected by a through-going bore/channel. This needle member 4 may be used to bring the needle member 4 into fluid contact with two vessel members (not shown) that can be inserted into the adaptor 20 from the same side. The first needle member 4' is arranged in a first chamber seal by a first seal 10, while the second needle member 4" is arranged in a second chamber seal by a second seal 12.

FIG. 8*c*) and FIG. 8*d*) illustrates adaptors 20 having needle members connected to a valve being in fluid communication with a pipe 70.

FIG. 8*e*) illustrates a spike-type needle member 4 with a through-going bore 72.

FIG. 8*f*) illustrates a needle member 4 having a first bore 72 and a second bore 72'.

Figure 9:
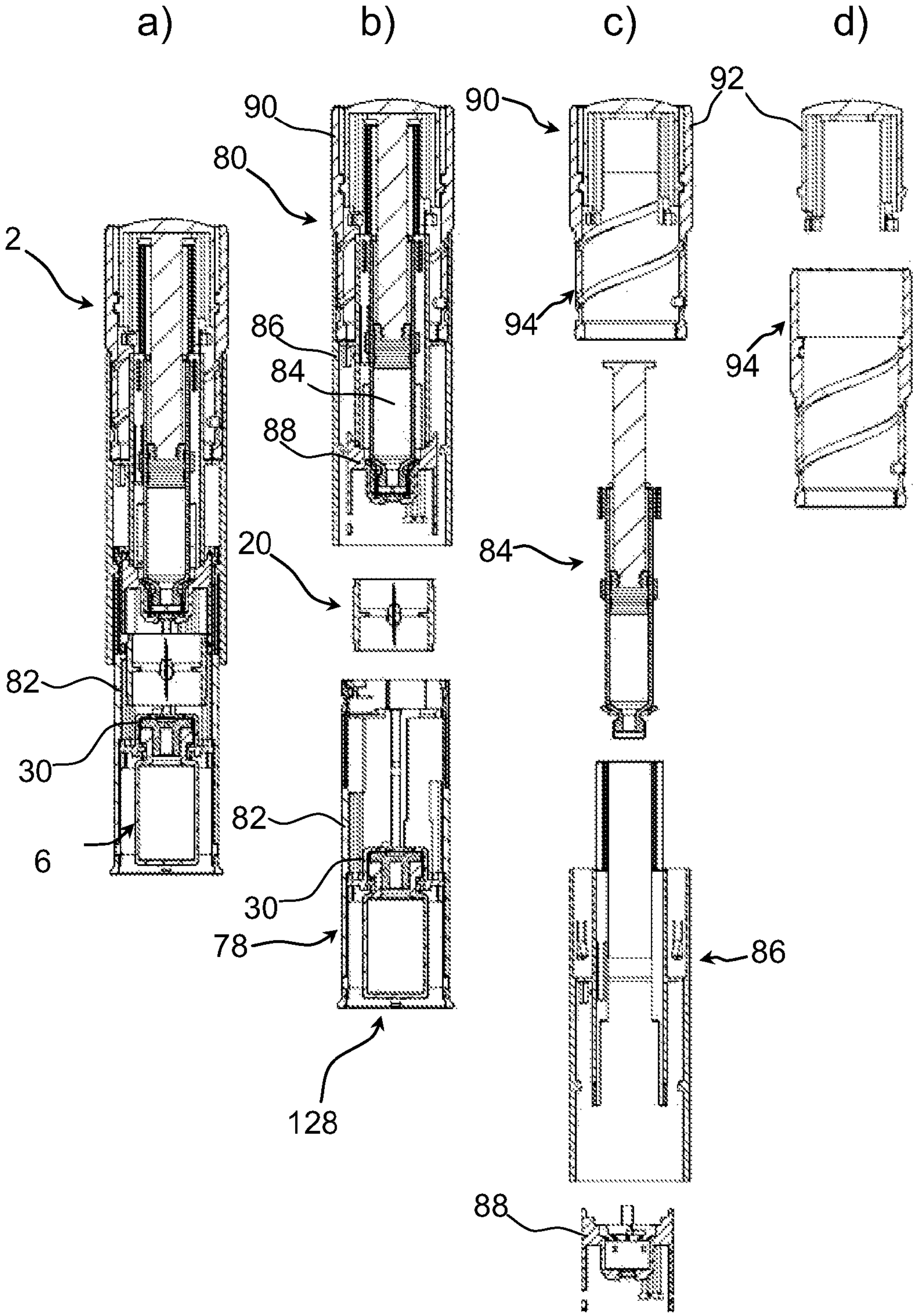
FIG. 9*a*-9*d* shows cross-sectional views of a device according to the invention.

FIG. 8*g*) illustrates a needle member 4 provided with a bore 72 and a vent 74, while FIG. 8*h*) illustrates a similar adaptor with a filter 76 arranged in the vent 74. FIG. 9 illustrates a device 2 according to the invention. The device 2 comprises a handle 80 having a button 90, with a button grip 92 and a rod actuator 94. The device moreover comprises a top chassis 86 to which the handle 80 is configured to be attached. The top chassis 86 is configured to receive and contain a syringe 84 and a lock member 88. The device 2 comprises an adaptor 20 configured to be sandwiched between the top chassis 86 and a base chassis 82 having a base 78. The base chassis 82 is configured to receive and contain a vial 6 at the lower end of its inside.

The button grip 92 is rotably mounted to the rod actuator 94. Rotation of the button grip 92 causes translation of the rod actuator 94 that hereby pushes against and thus activates the syringe 84.

Figure 10:
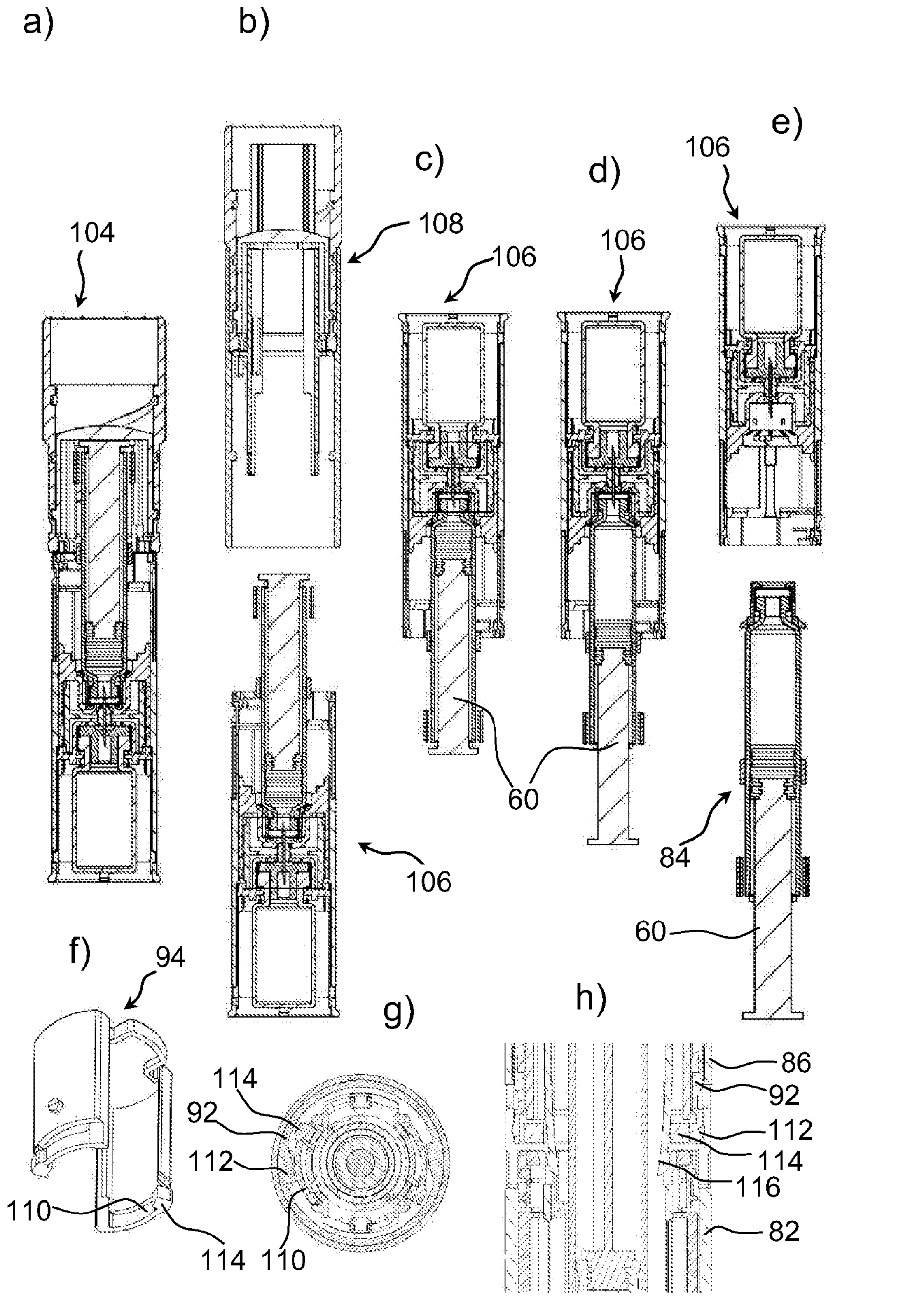
FIG. 10*a*-10*h* shows cross-sectional views of a device according to the invention.

FIG. 10 illustrates several other views of a device according the invention. FIG. 10*a*) illustrates a cross sectional view of a device in an assembled state.

In FIG. 10*b*) the upper part 108 of the device has been lifted up.

FIGS. 10*c*) and 10*d*) illustrates how the plunger rod 60 of the syringe can be reversed while the lower part 106 of the device is separated from the upper part 104 of the device.

FIG. 10*e*) illustrates a view in which the syringe 84 has been removed from the lower part 106 of the device.

FIG. 10*f*) illustrates a perspective view of the rod actuator 94 (also shown in FIG. 9). It can be seen that the rod actuator 94 comprises a flexible arm 110 provided with a plunger 114 at its end portion.

FIG. 10*g*) and FIG. 10*h*) illustrates cross-sectional views of the device. The rod actuator 94 is provided with two flexible arms 110 each provided with a plunger 114 at their distal end. As the button grip 92 rotates, the wedges 112 will get into contact with the plungers 114 on the flexible arms 110 on the rod actuator 94. The wedges 112 are configured to move the plungers 114 in direction of the hooks 116 and hereby open them. This action will unlock the top chassis 86 from the base chassis 82.

Figure 11:
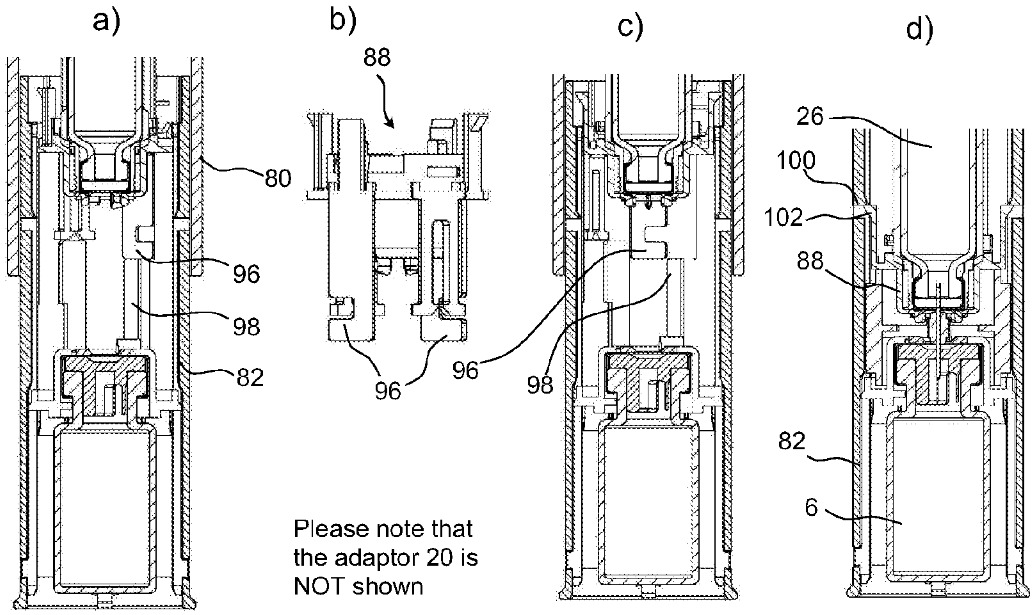
FIG. 11*a*-11*d* shows close-up cross-sectional views of a device according to the invention and FIG. 12*a*-12*g* shows cross-sectional views of a device according to the invention.

FIG. 11 illustrates schematically views of the device. Note that the adaptor has been removed for illustrating purposes.

The device as shown in FIG. 11*a*) is locked. A protrusion 96 on the lock member 88 sits on a rib 98 in the base chassis 82. By twisting the handle 80 a certain angle, the protrusion 96 turns away from the rib 98 and is hereafter free to translate downwards.

When the handle 80 has been pushed in direction of the base chassis 82, a number of snap locks 102 on the lock member 88 locks against a stop surface 100 in the base chassis 82. This lock member 88 will allow the user of the device to retract the plunger rod 60 without pulling the cartridge 26 away from the vial 6 on a later stage in the sequence.

Figure 12:
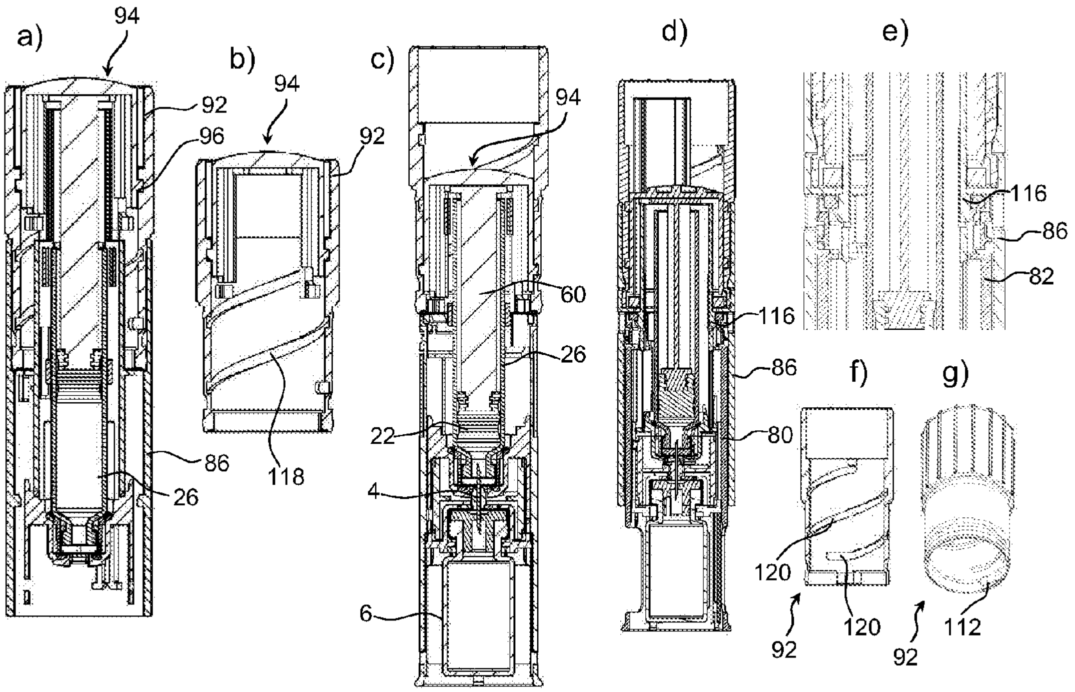

In FIGS. 12*a*), 12*b*) and 12*c*) the button grip 92 is mounted in a way so it is configured to rotate without being able to translate/slide relative to the top chassis 86. On the other hand the rod actuator 94 is mounted in way in which it is configured to translate but not to rotate relative to the top chassis 86.

The rod actuator 94 is provided with a number of protrusions 96 that are guided in a track 118 inside the button grip 92. When turning the button grip 92, the tracks 118 will pull the rod actuator 94 downwards.

The rod actuator 94 will accordingly push and hereby cause movement of the plunger rod 60 and the plunger 22 downwards in the cartridge 26. Hereby the medium (e.g. a diluent for reconstitution of lyophilizes medicinal drug) in the cartridge 26 will flow through the needle 4 into the vial 6.

FIGS. 12*d*) and 12*e*) illustrates that the top chassis 86 is axially locked to the base chassis 82 by means of a hook 116. The hook 116, however, allows rotation between the top chassis 86 and the base chassis 82.

In FIGS. 12*f*) and 12*g*) the button grip 92 is provided with a helical track 120. At the end of the helical track 120 there is a flat portion 122. Once the rod actuator 94 reaches the end of the helical portion, the plunger 22 has reached full stroke in the cartridge 26.

The flat portion 122 of the helical track 120 is used to unlock the top chassis 86 from the base chassis 82. The button grip 92 is provided with a wedge 112 configured to be used to open the hook 116 in the base chassis 82.

The parts of the device according to the invention may be produced in all suitable materials and by using all suitable manufacturing techniques.

LIST OF REFERENCE NUMERALS

2—Device
4, 4', 4"—Needle member
6—Vessel member
8~Septum
10—Seal
12—Seal
14—Housing
16—Base member
18—Holding member
20—Adaptor
22—Plunger
24—Septum
26—Cartridge
28—Upper surface
30, 30', 30"—Collar
32, 32'—Cutting edge
34—Pressing edge
36—Aperture
38—Opening
40—Opening
X, X'—Longitudinal axis
Y—Longitudinal axis
F—Force
42—Interface
44—Beam
46—Angled surface
48—Side surface
50—Front surface
52—Rail member
54—Plate member
56—Rib
58—Space
60—Plunger rod
62—Substance
64—Substance
66—Substance
68—Valve
70—Pipe
72—Bore or channel
74—Vent
76—Filter
78—Base
80—Handle
82—Base chassis
84—Syringe
86—Top chassis
88—Lock member
90—Button
92—Button grip
94—Rod actuator
96—Protrusion
98—Rib
100—Top surface
102—Snap lock
104—Device
106—Lower part
108—Upper part
110—Flexible arm
112—Wedge
114—Plunger
116—Hook
118—Track
120—Helical track
122—Flat portion
124—Arm
126—Midline
128—Lower end
e—End point
b—Break point
p—Apex point
$d_1$—Length
$d_2$—Length
$d_3$—Length
D—Width

We claim:

1. A device for bringing a first vessel member in fluid communication with a needle member, the device comprising:

a needle member;

an adaptor having a housing comprising a holding arrangement configured to secure the needle member to the housing, the housing having at least a seal and a first opening sealed by the seal; and cutting means configured to perforate the seal;

wherein the cutting means is configured to perforate the seal and break the seal by bringing the seal into contact with the cutting means by moving the adaptor towards the vessel member in a manner in which the needle member is not brought into contact with the seal;

a collar provided with protruding cutting edges and less protruding pressing edges, the collar being configured to be mounted on or integrated into a vessel member.

2. A device according to claim 1, wherein the needle member comprises a hollow needle or a hollow spike having at least one through-bore having a first opening and a second opening.

3. A device according to claim 1, wherein the at least a seal comprises a first seal and a second seal, and the adaptor comprises a second opening sealed by the second seal.

4. A device according to claim 1, wherein:
the adaptor comprises a sterile needle member; and
the adaptor is sealed in a manner so that the seal keeps the needle member sterile during storage.

5. A device according to claim 1, wherein the cutting means is mechanically attached to or integrated into the outside of the housing of the adaptor.

6. A device according to claim 1, wherein the adaptor and cutting means are mutually configured to move the cutting means along a longitudinal axis (X) of the adaptor and thereby break the seal.

7. A device according to claim 1, wherein the cutting means is configured to cut or break the seal approximately at a midline of the seal.

8. A device according to claim 1, wherein the cutting means is configured to cut or break the seal in a manner in which only a central portion of the seal is cut or broken.

9. A device according to claim 1, wherein:
the needle member has an apex and the seal has an end point at a periphery of the seal; and
the needle member is arranged in the adaptor so that a distance ($d_2$) between the apex of the needle member and the end point at the periphery of the seal is more than 5%, optionally more than 10%, larger than a distance ($d_1$) between a midpoint of the seal and the end point of the seal.

10. A device according to claim 1, wherein a distance ($d_3$) between the seal and the apex of the needle member is more than 5% of, optionally more than 10% of, a width (D) of the seal.

11. A device according to claim 1, wherein the needle member extends parallel to a direction (Y) in which the adaptor is configured to be moved in order to break the seal.

12. A device according to claim 1, further comprising:
means for preventing movement of the adaptor towards the vessel member during storage and thereby causing unintended breakage of the seal.

13. A device according to claim 1, wherein the adapter comprises:
a first end with an opening, configured to be connected to a first vessel member; and
a second end with an opening, configured to be connected to a second vessel member;
wherein the device is configured to be operated in a first state, in which the adaptor can be moved towards the first vessel member without moving the adaptor relative to the second vessel member, and is further configured to be operated in a second state following the first state, in which the adaptor can be moved towards the second vessel member without moving the adaptor relative to the first vessel.

14. A device according to claim 1, wherein the cutting means comprises two cutting edges that are configured to be arranged symmetrically about the needle member when the cutting means are brought into contact with the seal.

15. A device according to claim 1, further comprising:
means for reconstituting a lyophilized medicinal drug powder contained in a first vessel member with a fluid diluent contained in a second vessel member by connecting and mixing the two substances through an adaptor; and
means for delivering the diluent in a controlled slow manner, to avoid foaming during reconstitution with the lyophilized medicinal drug powder by requiring a rotational user activation of a plunger rod actuator.

16. A device according to claim 1, further comprising:
a base having a base chassis having an open end and a lower end, which base chassis is configured to receive and contain a vessel member at its lower end;
wherein the adaptor contains the needle member, with the first opening sealed by the seal, and further comprising a second seal and a second opening sealed by the second seal; and
a hand operable handle configured to engage with the base while sandwiching the adaptor between the handle and the base;
wherein the handle comprises a button with a grip and a top chassis configured to receive and be mechanically connected to the button grip, wherein the handle is configured to receive and contain a syringe when sandwiched between the button grip and the top chassis, wherein the button comprises a plunger rod actuator translatably mounted in the handle so that it is restricted from being rotated relative to the top chassis, and wherein the button grip is rotatably mounted in the handle so that it is restricted from being translated relative to the top chassis so that rotation of the button grip causes translation of the rod actuator which thereby activates syringe.

* * * * *